(12) United States Patent
Chatterton

(10) Patent No.: US 9,233,170 B2
(45) Date of Patent: *Jan. 12, 2016

(54) INTERFERING RNA DELIVERY SYSTEM AND USES THEREOF

(71) Applicant: Arrowhead Research Corporation, Pasadena, CA (US)

(72) Inventor: Jon E. Chatterton, Fort Worth, TX (US)

(73) Assignee: Arrowhead Research Corporation, Pasadena, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/158,179

(22) Filed: Jan. 17, 2014

(65) Prior Publication Data

US 2014/0135267 A1    May 15, 2014

Related U.S. Application Data

(62) Division of application No. 12/967,182, filed on Dec. 14, 2010, now Pat. No. 8,664,375, which is a division of application No. 12/338,252, filed on Dec. 18, 2008, now Pat. No. 7,879,813.

(60) Provisional application No. 61/014,472, filed on Dec. 18, 2007.

(51) Int. Cl.
*C12N 15/11* (2006.01)
*A61K 47/48* (2006.01)

(52) U.S. Cl.
CPC ..... *A61K 47/48323* (2013.01); *A61K 47/48315* (2013.01)

(58) Field of Classification Search
CPC .................... C12N 2310/14; C12N 2310/3513
See application file for complete search history.

(56) References Cited

U.S. PATENT DOCUMENTS

| 6,472,507 | B1 | 10/2002 | Fischer et al. | |
|---|---|---|---|---|
| 7,579,318 | B2 | 8/2009 | Divita et al. | |
| 8,664,375 | B2 * | 3/2014 | Chatterton | 536/24.5 |
| 8,937,051 | B2 * | 1/2015 | Chatterton | 514/44 A |
| 2005/0020525 | A1 | 1/2005 | McSwiggen et al. | |
| 2006/0172963 | A1 | 8/2006 | Shepard et al. | |
| 2007/0128116 | A1 | 6/2007 | Wang et al. | |
| 2008/0199960 | A1 | 8/2008 | Juliano et al. | |
| 2009/0131358 | A1 | 5/2009 | Chatterton | |

FOREIGN PATENT DOCUMENTS

| WO | 2005117991 A2 | 12/2005 |
|---|---|---|
| WO | 2006046978 A2 | 5/2006 |
| WO | 2008022046 A2 | 2/2008 |

OTHER PUBLICATIONS

Abes et al; "Efficient splicing correction by PNA conjugation to an R6-penetratin delivery peptide"; Nucleic Acids Research; vol. 35; No. 13; pp. 4495-4502 (2007).
Andreev et al; "Mechanism and uses of a membrane peptide that targets tumors and other acidic tissues in vivo"; PNAS; vol. 104; No. 19.; pp. 7893-7898 (May 8, 2007).
Bullok et al; "Permeation peptide conjugates for in vivo molecular imaging applications" Molecular Imaging; vol. 5; No. 1; pp. 1-15 (Jan. 2006).
Jarver and Langel; "The use of cell-penetrating peptides as a tool for gene regulation"; Drug Discovery Today; vol. 9; pp. 395-402 (2004).
Johnson et al; "Cell-penetrating peptide for enhanced delivery of nucleic and drugs to ocular tissues including retina and cornea"; Molecular Therapy; vol. 16; No. 1; pp. 107-114 (Jan. 2008).
Meade and Dowdy; "Exogenous siRNA delivery using peptide transduction domains/cell penetrating peptides"; Advanced Drug Delivery Reviews; vol. 59; pp. 134-140 (2007).
Muratovska and Eccles; "Conjugate for efficient delivery of short interfering RNA (siRNA) into mammalian cells" FEBS Letters: vol. 558; pp. 63-68 (2004).
Simeoni et al; "Insight into the mechanism of the peptide-based gene delivery system MPG: implications for delivery of siRNA into mammalian cells"; Nucleic Acids Research; vol. 31; No. 11; pp. 2717-2724 (2003).
Wadia and Dowdy; "Modulation of cellular function by TAT mediated transduction of full length proteins"; Current Protein and Peptide Science; vol. 4; pp. 97-104 (2003).
Search Report; corresponding PCT application No. PCT/US2008/087473 dated Apr. 7, 2009.
Elbashir et al; "RNA interference is mediated by 21- and 22-nucleotide RNAs"; Genes & Development; vol. 15; pp. 188-200 (2001).
Fire et al; "Potent and specific genetic interfernce by double-stranded RNA in caenorhabditis elegans"; Letters to Nature; Nature; vol. 391; pp. 806-811 (Feb. 19, 1998).
Kumar et al; "Transvascular delivery of small interfering RNA to the central nervous system"; Nature; vol. 448; doi:10.1038; pp. 39-43; (Jul. 2007).
Pang et al; "Preliminary characterization of a transformed cell strain derived from human trabecular meshwork"; Current Eye Research; vol. 13; No. 1; pp. 51-63 (1994).
Wadia et al; "Transducible TAT-HA fusogenic peptide enhances escape of TAT-fusion proteins after lipid raft macropinocytosis"; Nature Medicine; Technical Reports; vol. 10; No. 3: pp. 310-315 (Mar. 2004).

* cited by examiner

*Primary Examiner* — Brian Whiteman

(57) ABSTRACT

The invention provides a delivery system comprising a cell penetrating peptide, a polyarginine peptide, and an interfering RNA molecule. The system can be used for delivering interfering RNA molecules into a cell in vivo or in vitro. Therapeutic uses for the delivery system are also provided.

12 Claims, 4 Drawing Sheets

INTERFERING RNA DELIVERY SYSTEM AND USES THEREOF

CROSS-REFERENCE TO RELATED APPLICATION

The present application is a divisional of U.S. patent application Ser. No. 12/967,182 filed Dec. 14, 2010, issued as U.S. Pat. No. 8,664,375, which claims benefit to U.S. patent application Ser. No. 12/338,252 filed Dec. 18, 2008, issued as U.S. Pat. No. 7,879,813, which claims benefit to U.S. Provisional Patent Application Ser. No. 61/014,472 filed Dec. 18, 2007, the entire contents of which are incorporated herein by reference.

FIELD OF THE INVENTION

The invention relates to a delivery system for delivering interfering RNA molecules into a cell and methods for using the delivery system. The delivery system comprises a TAT peptide, or other cell-penetrating peptide, and a polyarginine peptide, such as a 9×Arg peptide. The delivery system can be administered to a cell in the presence of an HA2 peptide, which can be incorporated into the system or administered concurrently with the system.

BACKGROUND OF THE INVENTION

RNA interference (RNAi) is a process by which double-stranded RNA (dsRNA) is used to silence gene expression. RNAi is induced by short (i.e. <30 nucleotide) double stranded RNA ("dsRNA") molecules which are present in the cell (Fire et al., 1998, *Nature* 391:806-811). These short dsRNA molecules called "short interfering RNA" or "siRNA," cause the destruction of messenger RNAs ("mRNAs") which share sequence homology with the siRNA (Elbashir et al., 2001, *Genes Dev*, 15:188-200). It is believed that one strand of the siRNA is incorporated into a ribonucleoprotein complex known as the RNA-induced silencing complex (RISC). RISC uses this siRNA strand to identify mRNA molecules that are at least partially complementary to the incorporated siRNA strand, and then cleaves these target mRNAs or inhibits their translation. The siRNA is apparently recycled much like a multiple-turnover enzyme, with 1 siRNA molecule capable of inducing cleavage of approximately 1000 mRNA molecules. siRNA-mediated RNAi degradation of an mRNA is therefore more effective than currently available technologies for inhibiting expression of a target gene.

RNAi provides a very exciting approach to treating and/or preventing diseases. Some major benefits of RNAi compared with various traditional therapeutic approaches include: the ability of RNAi to target a very particular gene involved in the disease process with high specificity, thereby reducing or eliminating off target effects; RNAi is a normal cellular process leading to a highly specific RNA degradation; and RNAi does not trigger a host immune response as in many antibody based therapies.

Several interfering RNA delivery methods are being tested/developed for in vivo use. For example, siRNAs can be delivered "naked" in saline solution; complexed with polycations, cationic lipids/lipid transfection reagents, or cationic peptides; as components of defined molecular conjugates (e.g., cholesterol-modified siRNA, TAT-DRBD/siRNA complexes); as components of liposomes; and as components of nanoparticles. These approaches have shown varying degrees of success. Thus, there remains a need for new and improved methods for delivering siRNA molecules in vivo to achieve and enhance the therapeutic potential of RNAi.

Several cell-penetrating peptides (CPPs) or membrane permeant peptides (MPPs) have been described (Jarver and Langel, 2004, *Drug Discov Today* 9:395-402) as conjugates to deliver peptides into cells. The protein transduction domain (PTD) of the HIV-1 TAT protein is a CPP that appears to be particularly effective. The TAT peptide has been used to deliver biologically active cargo to cells in vitro and in vivo (Wadia and Dowdy, 2003, *Curr Protein Pept Sci.* 4:97-104; Bullok et al., 2006, *Mol Imaging* 5:1-15).

Several groups have explored the use of CPPs to deliver interfering RNA molecules (See Meade and Dowdy, 2007, *Adv Drug Deliv Rev.* 59:134-140). The main challenge to this approach involves linking the interfering RNA to the CPPs while maintaining the ability of the complex to interact with and enter the intracellular environment. In particular, the negative charge of the interfering RNA neutralizes the positively charged CPPs, which renders such complexes incapable of cellular delivery. Thus, there is a need to identify ways to link CPPs to interfering RNA molecules without hindering the ability of the CPP to facilitate intracellular delivery of the interfering RNA.

SUMMARY OF THE INVENTION

The invention provides an interfering RNA delivery system comprising an interfering RNA molecule linked to a CPP-Arg peptide, such as a TAT-9×Arg peptide. The invention also provides a method for delivering an interfering RNA molecule into a cell, in vitro or in vivo, comprising: (a) attaching an interfering RNA molecule to a CPP-Arg peptide, thereby forming an interfering RNA delivery system; and administering the system to the cell under conditions suitable for the system to enter the cell. In certain aspects, the delivery system is administered to a cell in the presence of an HA2 peptide, which aids release of the system from the endosome. The HA2 peptide can be incorporated into the delivery system or administered before, after, or with administration of the delivery system.

In one aspect, an interfering RNA molecule in a delivery system of the invention can attenuate expression of a target mRNA in a target cell. Thus, the invention provides methods for attenuating expression of a target mRNA in a cell comprising administering a delivery system of the invention to the cell.

The invention further provides pharmaceutical compositions comprising an interfering RNA delivery system of the invention. The pharmaceutical compositions can be used in therapeutic applications to treat various disorders or diseases in which inhibition of a target gene is desired.

In addition, the invention provides methods of treating or preventing an ocular disorder in a patient, comprising administering to the patient an interfering RNA delivery system as described herein to the patient, wherein the interfering RNA molecule can attenuate expression of a gene associated with the ocular disorder. In certain aspects, the ocular disorder is associated with ocular angiogenesis, dry eye, ocular inflammatory conditions, ocular hypertension, or glaucoma. In other aspects, the conjugate is administered by intraocular injection, ocular topical application, subconjunctival injection, intravitreal injection, anterior or posterior juxtascleral injection, intravenous injection, oral administration, intramuscular injection, intraperitoneal injection, transdermal application, intranasal application, or transmucosal application.

Specific preferred embodiments of the invention will become evident from the following more detailed description of certain preferred embodiments and the claims.

DETAILED DESCRIPTION OF THE INVENTION

Figure 1A:
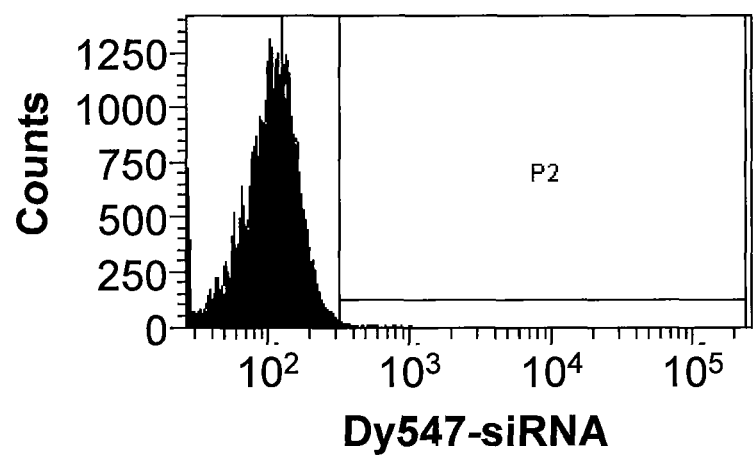
FIG. 1A depicts results of FACS analysis of non-treated GTM-3 cells.
Figure 1B:
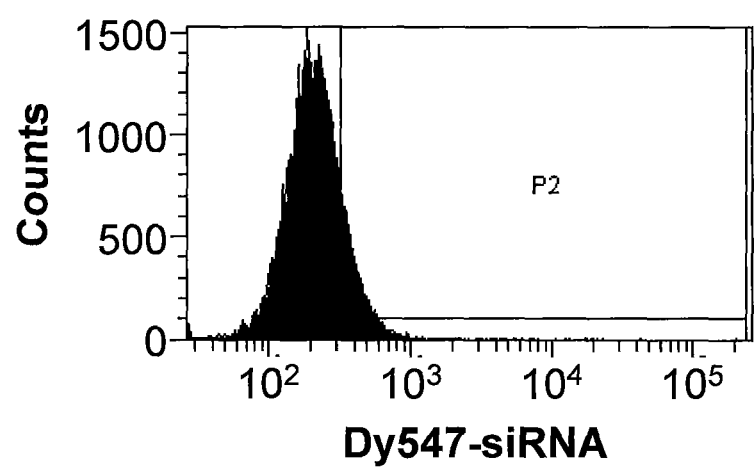
FIG. 1B depicts results of FACS analysis of GTM-3 cells treated with an siRNA labeled with Dy547 (Dy547-siRNA).
Figure 1C:
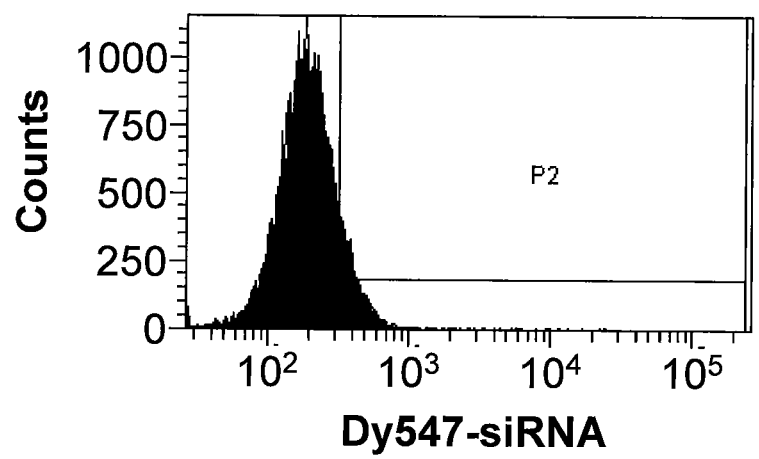
FIG. 1C depicts results of FACS analysis of GTM-3 cells treated with 9×Arg/Dy547-siRNA.
Figure 1D:
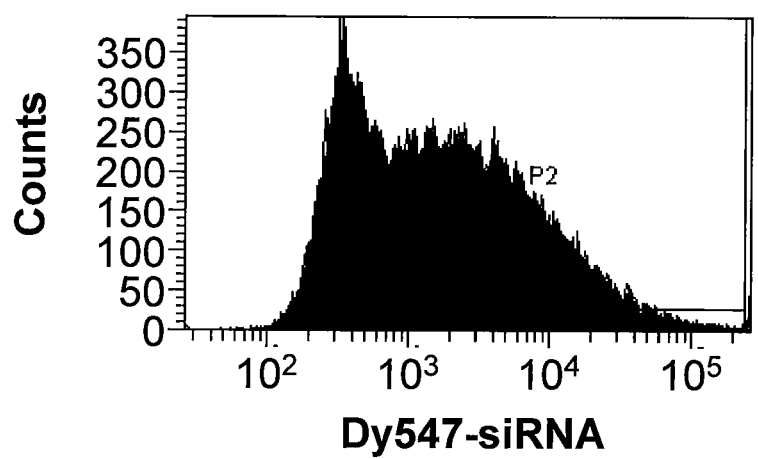
FIG. 1D depicts results of FACS analysis of GTM-3 cells treated with Pen7-9×Arg/Dy547-siRNA.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

The following definitions and explanations are meant and intended to be controlling in any future construction unless clearly and unambiguously modified in the following examples or when application of the meaning renders any construction meaningless or essentially meaningless. In cases where the construction of the term would render it meaningless or essentially meaningless, the definition should be taken from Webster's Dictionary, 3$^{rd}$ Edition or a dictionary known to those of skill in the art, such as the Oxford Dictionary of Biochemistry and Molecular Biology (Ed. Anthony Smith, Oxford University Press, Oxford, 2004).

As used herein, all percentages are percentages by weight, unless stated otherwise.

As used herein and unless otherwise indicated, the terms "a" and "an" are taken to mean "one", "at least one" or "one or more". Unless otherwise required by context, singular terms used herein shall include pluralities and plural terms shall include the singular.

In certain embodiments, the invention provides an interfering RNA delivery system comprising an interfering RNA molecule linked to a cell penetrating peptide (CPP) via an Arg peptide.

As used herein, the phrase "interfering RNA delivery system" refers to a system that comprises a CPP, an Arg peptide, and an interfering RNA molecule, which is capable of delivering the interfering RNA molecule into a cell. In certain embodiments, the interfering RNA delivery system can be administered to a subject in need thereof.

The term "CPP-Arg peptide" as used herein refers to a peptide comprising a CPP linked to an Arg peptide. For example, a "TAT-Arg peptide" means a peptide comprising a TAT peptide linked to an Arg peptide.

An "Arg peptide" or "polyarginine" is a peptide consisting entirely of arginines. Preferably, the Arg peptide comprises 7, 8, 9, 10, or 11 arginines. In certain embodiments, the Arg peptide will be linked to the C- or N-terminus of TAT via a glycine spacer of 1, 2, 3, or 4 glycines. Preferably, the glycine spacer is 2 or 3 glycines.

In one embodiment, the Arg peptide is a 9×Arg peptide. The term "9×Arg peptide" as used herein means a peptide comprising 9 arginine residues (RRRRRRRRR; SEQ ID NO: 1). In one embodiment, the 9×Arg peptide comprises or consists of D-isomers. Negatively charged interfering RNA molecules can bind to the positively charged 9×Arg peptide as described in Kumar et al., who recently demonstrated that a 9×Arg peptide could be used to link interfering RNA molecules to the C-terminal end of a rabies virus glycoprotein (RVG) targeting peptide for delivery across the blood-brain barrier (Kumar et al., Jun. 17, 2007, *Nature*, epub ahead of print).

The terms "cell penetrating peptide" and "CPP" as used herein refer to peptides, typically of about 9 to about 30 amino acid residues, capable of being internalized by a mammalian cell. For example, a CPP can be a protein transduction domain or a fragment thereof, as discussed below. In most instances, a CPP enters the intracellular environment by endocytosis. In other instances, a CPP may remain in the cell membrane, while facilitating its cargo to enter the cell. Examples of useful CPPs include, but are not limited to, the TAT peptide, and the protein transduction domains of Penetratin (pAntp), Transportan, MPG, MPGdeltaNLS, and pHLIP. Cell penetrating fragments of CPPs can also be used in a delivery system and/or method of the invention. As used herein, the term CPP includes cell penetrating fragments of protein transduction domains.

In certain embodiments, a CPP can comprise or consist of D-amino acids and/or L-amino acids. For example, a CPP can consist entirely of D-amino acids or entirely of L-amino acids; or a CPP can comprise a mixture of D- and L-amino acids.

In certain embodiments, the amino acid sequence of a CPP can be in the forward direction (i.e. a native peptide) or in the reverse direction. As used herein, reference to a CPP includes both the native and reverse sequences. In one embodiment, the reverse sequence can be a retro-inverso peptide (i.e. the amino acid sequence is the reverse of the native sequence, and consists of D-amino acids). For example, the term "TAT peptide" as used herein includes a retro-inverso TAT peptide comprising a reverse sequence of the protein transduction domain (PTD) of the HIV-1 TAT protein, as illustrated below. The native sequence PTD of TAT is:

SEQ ID NO: 2
YGRKKRRQRRR;

(Vives et al., 1997, *J. Biol. Chem* 272:16010).

A retro-inverso TAT peptide (i.e., the reverse sequence constructed of D-amino acids) is:

SEQ ID NO: 3
R$^†$R$^†$R$^†$Q$^†$R$^†$R$^†$K$^†$K$^†$R$^†$G$^†$;.

D-isomers are denoted by a superscripted dagger ($^†$) to the right of the one-letter code symbol; thus, D$^†$ represents D-aspartic acid and L$^†$ represents D-leucine.

The PTD of Penetratin (pAntp) is:

SEQ ID NO: 4
RQIKIWFQNRRMKWKK;

(Muratovska and Eccles, 2004,

*FEBS Letters* 558:63-68).

The PTD of Transportan is:

```
                                            SEQ ID NO:5
LIKKALAALAKLNIKLLYGASNLTWG;

(Muratovska and Eccles, 2004,

FEBS Letters 558:63-68).
```

The PTD of MPG is:

```
                                            SEQ ID NO: 6
GALFLGFLGAAGSTMGAWSQPKKKRKV;

(Simeoni et al., 2003,

Nucl. Acids Res. 31:2717-2724).
```

The PTD of MPGdeltaNLS is:

```
                                            SEQ ID NO: 7
GALFLGFLGAAGSTMGAWSQPKSKRKV;

(Simeoni et al., 2003,

Nucl. Acids Res. 31:2717-2724).
```

The PTD of pHLIP is:

```
                                            SEQ ID NO: 8
ACEQNPIYWARYADWLFTTPLLLLDLALLVDADEGTG;

(Andreev et al., 2007, Proc. Natl. Acad. Sci. USA

104:7893-7899).
```

In certain embodiments, an interfering RNA delivery system is administered to a subject or a cell in the presence of a TAT-HA2 peptide, a ligand-HA2 peptide, or a retro-inverso TAT-HA2 peptide, which has been shown to enhance release of TAT-peptide/protein from the endosome (Wadia et al., 2004, *Nat. Med.* 10:310). The term "HA2 peptide" means a peptide comprising the N-terminal 20 amino acids of influenza virus hemagglutinin protein. The native HA2 peptide is:

```
                                            SEQ ID NO: 9
GLFGAIAGFIENGWEGMIDG;.
```

Preferably, the native HA2 peptide comprises L-isomers, but may be constructed to comprise or consist of D-amino acids.

The retro-inverso HA2 peptide is:

```
                                            SEQ ID NO: 10
GD'I'M'GE'W'GN'E'I'F'GA'I'A'GF'L'G;.
```

The retro-inverso HA2 peptide may comprise or consist of D-amino acids.

The presence of HA2 aids release of the interfering RNA delivery system from the endosome into the cytosol, so that the interfering RNA molecular can attenuate expression of a target mRNA in the subject or cell. In certain other embodiments, an HA2 peptide is inserted between the CPP peptide and a 9×Arg, wherein the HA2 peptide is linked to the 9×Arg via a glycine spacer. For example, where TAT is the CPP, the sequence may be as follows:

```
                                            SEQ ID NO: 11
R'R'R'Q'R'R'K'K'R'GGGD'I'M'GE'W'GN'E'I'F'GA'I'A'GF'L'GGG

R'R'R'R'R'R'R'R';.
```

In certain embodiments, the CPP-Arg peptide is produced as a single peptide before being conjugated to the interfering RNA molecule. In other embodiments, the CPP-Arg peptide can be produced by combining the CPP (or CPP-HA2) peptide and the Arg peptide under conditions in which the two peptides will connect to each other. Such methods for linking two peptides are well known in the art. In yet other embodiments, the Arg peptide can be premixed with the interfering RNA molecule and then linked to the CPP (or CPP-HA2) peptide to favor binding of the interfering RNA to the Arg end of the peptide. Thus, linkage of the interfering RNA molecule can be accomplished before or after linkage of CPP (or CPP-HA2) with Arg.

In certain embodiments, an interfering RNA delivery system as described herein can be used in a method of delivering an interfering RNA molecule into a cell. The cell can be an isolated cell (e.g. in cell culture) or associated with a subject in which inhibiting expression of a target gene is desired. The cell may also be used in a ex vivo therapeutic method, in which the cell is taken from a subject and reintroduced into the same or a different subject after the interfering RNA delivery system has been introduced into the cell.

As used herein, the term "subject" or "patient" refers to human and non-human animals. The term "non-human animals" refers to vertebrates and non-vertebrates, including but, not limited to, primates, rabbits, pigs, horses, dogs, cats, sheep, and cows. In one embodiment, a patient has an ocular disorder or is at risk of having an ocular disorder. Ocular structures associated with such disorders may include the eye, retina, choroid, lens, cornea, trabecular meshwork, iris, optic nerve, optic nerve head, sclera, anterior or posterior segment, or ciliary body, for example. In certain embodiments, a patient has an ocular disorder associated with trabecular meshwork (TM) cells, ciliary epithelium cells, or another cell type of the eye.

The term "ocular disorder" as used herein includes conditions associated with ocular angiogenesis, dry eye, inflammatory conditions, ocular hypertension and ocular diseases associated with elevated intraocular pressure (TOP), such as glaucoma.

The term "ocular angiogenesis," as used herein, includes ocular pre-angiogenic conditions and ocular angiogenic conditions, and includes ocular angiogenesis, ocular neovascularization, retinal edema, diabetic retinopathy, sequela associated with retinal ischemia, posterior segment neovascularization (PSNV), and neovascular glaucoma, for example. The interfering RNAs used in a method of the invention are useful for treating patients with ocular angiogenesis, ocular neovasularization, retinal edema, diabetic retinopathy, sequela associated with retinal ischemia, posterior segment neovascularization (PSNV), and neovascular glaucoma, or patients at risk of developing such conditions, for example. The term "ocular neovascularization" includes age-related macular degeneration, cataract, acute ischemic optic neuropathy (AION), commotio retinae, retinal detachment, retinal tears or holes, iatrogenic retinopathy and other ischemic retinopathies or optic neuropathies, myopia, retinitis pigmentosa, and/or the like.

The term "inflammatory condition," as used herein, includes conditions such as ocular inflammation and allergic conjunctivitis.

The interfering RNA delivery system of the invention is useful for attenuating expression of particular genes in a patient (i.e. subject) using RNA interference.

RNA interference (RNAi) is a process by which double-stranded RNA (dsRNA) is used to silence gene expression. While not wanting to be bound by theory, RNAi begins with the cleavage of longer dsRNAs into small interfering RNAs (siRNAs) by an RNaseIII-like enzyme, dicer. siRNAs are dsRNAs that are usually about 19 to 28 nucleotides, or 20 to 25 nucleotides, or 21 to 22 nucleotides in length and often contain 2-nucleotide 3' overhangs, and 5' phosphate and 3' hydroxyl termini. One strand of the siRNA is incorporated into a ribonucleoprotein complex known as the RNA-induced silencing complex (RISC). RISC uses this siRNA strand to identify mRNA molecules that are at least partially complementary to the incorporated siRNA strand, and then cleaves these target mRNAs or inhibits their translation. Therefore, the siRNA strand that is incorporated into RISC is known as the guide strand or the antisense strand. The other siRNA strand, known as the passenger strand or the sense strand, is eliminated from the siRNA and is at least partially homologous to the target mRNA. Those of skill in the art will recognize that, in principle, either strand of an siRNA can be incorporated into RISC and function as a guide strand. However, siRNA design (e.g., decreased siRNA duplex stability at the 5' end of the desired guide strand) can favor incorporation of the desired guide strand into RISC.

The antisense strand of an siRNA is the active guiding agent of the siRNA in that the antisense strand is incorporated into RISC, thus allowing RISC to identify target mRNAs with at least partial complementarity to the antisense siRNA strand for cleavage or translational repression. RISC-mediated cleavage of mRNAs having a sequence at least partially complementary to the guide strand leads to a decrease in the steady state level of that mRNA and of the corresponding protein encoded by this mRNA. Alternatively, RISC can also decrease expression of the corresponding protein via translational repression without cleavage of the target mRNA.

Interfering RNAs appear to act in a catalytic manner for cleavage of target mRNA, i.e., interfering RNA is able to effect inhibition of target mRNA in substoichiometric amounts. As compared to antisense therapies, significantly less interfering RNA is required to provide a therapeutic effect under such cleavage conditions.

In certain embodiments, the invention provides methods of delivering interfering RNA to inhibit the expression of a target mRNA thus decreasing target mRNA levels in patients with target mRNA-related disorders.

The phrase "attenuating expression" with reference to a gene or an mRNA as used herein means administering or expressing an amount of interfering RNA (e.g., an siRNA) to reduce translation of a target mRNA into protein, either through mRNA cleavage or through direct inhibition of translation. The terms "inhibit," "silencing," and "attenuating" as used herein refer to a measurable reduction in expression of a target mRNA or the corresponding protein as compared with the expression of the target mRNA or the corresponding protein in the absence of an interfering RNA of the invention. The reduction in expression of the target mRNA or the corresponding protein is commonly referred to as "knock-down" and is reported relative to levels present following administration or expression of a non-targeting control RNA (e.g., a non-targeting control siRNA). Knock-down of expression of an amount including and between 50% and 100% is contemplated by embodiments herein. However, it is not necessary that such knock-down levels be achieved for purposes of the present invention.

Knock-down is commonly assessed by measuring the mRNA levels using quantitative polymerase chain reaction (qPCR) amplification or by measuring protein levels by western blot or enzyme-linked immunosorbent assay (ELISA). Analyzing the protein level provides an assessment of both mRNA cleavage as well as translation inhibition. Further techniques for measuring knock-down include RNA solution hybridization, nuclease protection, northern hybridization, gene expression monitoring with a microarray, antibody binding, radioimmunoassay, and fluorescence activated cell analysis.

Attenuating expression of a target gene by an interfering RNA molecule of the invention can be inferred in a human or other mammal by observing an improvement in symptoms of the disorder.

In one embodiment, a single interfering RNA is delivered to decrease target mRNA levels. In other embodiments, two or more interfering RNAs targeting the mRNA are administered to decrease target mRNA levels. The interfering RNAs may be delivered through linkage to the same CPP-Arg peptide or through linkage to separate CPP-Arg peptide(s) (e.g. each interfering RNA can be pre-mixed and added to CPP-Arg or each interfering RNA can be independently mixed with CPP-Arg, followed by combining the individual interfering RNA/CPP-Arg complexes).

As used herein, the terms "interfering RNA" and "interfering RNA molecule" refer to all RNA or RNA-like molecules that can interact with RISC and participate in RISC-mediated changes in gene expression. Examples of other interfering RNA molecules that can interact with RISC include short hairpin RNAs (shRNAs), single-stranded siRNAs, microRNAs (miRNAs), picoRNAs (piRNAs), and dicer-substrate 27-mer duplexes. Examples of "RNA-like" molecules that can interact with RISC include siRNA, single-stranded siRNA, miRNA, piRNA, and shRNA molecules that contain one or more chemically modified nucleotides, one or more non-nucleotides, one or more deoxyribonucleotides, and/or one or more non-phosphodiester linkages. Thus, siRNAs, single-stranded siRNAs, shRNAs, miRNAs, piRNA, and dicer-substrate 27-mer duplexes are subsets of "interfering RNAs" or "interfering RNA molecules."

The term "siRNA" as used herein refers to a double-stranded interfering RNA unless otherwise noted. Typically, an siRNA used in a method of the invention is a double-stranded nucleic acid molecule comprising two nucleotide strands, each strand having about 19 to about 28 nucleotides (i.e. about 19, 20, 21, 22, 23, 24, 25, 26, 27, or 28 nucleotides). Typically, an interfering RNA used in a method of the invention has a length of about 19 to 49 nucleotides. The phrase "length of 19 to 49 nucleotides" when referring to a double-stranded interfering RNA means that the antisense and sense strands independently have a length of about 19 to about 49 nucleotides, including interfering RNA molecules where the sense and antisense strands are connected by a linker molecule.

The interfering RNA used in a delivery system and method of the invention can be unmodified or can be chemically stabilized to prevent degradation in the lysosome or other compartments in the endocytic pathway.

Single-stranded interfering RNA has been found to effect mRNA silencing, albeit less efficiently than double-stranded RNA. Therefore, embodiments of the present invention also provide for administration of a single-stranded interfering RNA. The single-stranded interfering RNA has a length of about 19 to about 49 nucleotides as for the double-stranded interfering RNA cited above. The single-stranded interfering RNA has a 5' phosphate or is phosphorylated in situ or in vivo at the 5' position. The term "5' phosphorylated" is used to describe, for example, polynucleotides or oligonucleotides having a phosphate group attached via ester linkage to the C5 hydroxyl of the sugar (e.g., ribose, deoxyribose, or an analog of same) at the 5' end of the polynucleotide or oligonucleotide.

Single-stranded interfering RNAs can be synthesized chemically or by in vitro transcription or expressed endogenously from vectors or expression cassettes as described herein in reference to double-stranded interfering RNAs. 5' Phosphate groups may be added via a kinase, or a 5' phosphate may be the result of nuclease cleavage of an RNA. A hairpin interfering RNA is a single molecule (e.g., a single oligonucleotide chain) that comprises both the sense and antisense strands of an interfering RNA in a stem-loop or hairpin structure (e.g., a shRNA). For example, shRNAs can be expressed from DNA vectors in which the DNA oligonucleotides encoding a sense interfering RNA strand are linked to the DNA oligonucleotides encoding the reverse complementary antisense interfering RNA strand by a short spacer. If needed for the chosen expression vector, 3' terminal T's and nucleotides forming restriction sites may be added. The resulting RNA transcript folds back onto itself to form a stem-loop structure.

Interfering RNAs may differ from naturally-occurring RNA by the addition, deletion, substitution or modification of one or more nucleotides. Non-nucleotide material may be bound to the interfering RNA, either at the 5' end, the 3' end, or internally. Such modifications are commonly designed to increase the nuclease resistance of the interfering RNAs, to improve cellular uptake, to enhance cellular targeting, to assist in tracing the interfering RNA, to further improve stability, to reduce off-target effects, or to reduce the potential for activation of the interferon pathway. For example, interfering RNAs may comprise a purine nucleotide at the ends of overhangs. Conjugation of cholesterol to the 3' end of the sense strand of an siRNA molecule by means of a pyrrolidine linker, for example, also provides stability to an siRNA.

Further modifications include a biotin molecule, a peptidomimetic, a fluorescent dye, or a dendrimer, for example.

Nucleotides may be modified on their base portion, on their sugar portion, or on the phosphate portion of the molecule and function in embodiments of the present invention. Modifications include substitutions with alkyl, alkoxy, amino, deaza, halo, hydroxyl, thiol groups, or a combination thereof, for example. Nucleotides may be substituted with analogs with greater stability such as replacing a ribonucleotide with a deoxyribonucleotide, or having sugar modifications such as 2' OH groups replaced by 2' amino groups, 2' O-methyl groups, 2' methoxyethyl groups, or a 2'-O, 4'-C methylene bridge, for example. Examples of a purine or pyrimidine analog of nucleotides include a xanthine, a hypoxanthine, an azapurine, a methylthioadenine, 7-deaza-adenosine and O- and N-modified nucleotides. The phosphate group of the nucleotide may be modified by substituting one or more of the oxygens of the phosphate group with nitrogen or with sulfur (phosphorothioates). Modifications are useful, for example, to enhance function, to improve stability or permeability, to reduce off-target effects, or to direct localization or targeting.

In certain embodiments, an interfering molecule of the invention comprises at least one of the modifications as described above.

The phrases "target sequence" and "target mRNA" as used herein refer to the mRNA or the portion of the mRNA sequence that can be recognized by an interfering RNA used in a method of the invention, whereby the interfering RNA can silence gene expression as discussed herein. Techniques for selecting target sequences for siRNAs are provided, for example, by Tuschl, T. et al., "The siRNA User Guide," revised May 6, 2004, available on the Rockefeller University web site; by Technical Bulletin #506, "siRNA Design Guidelines," Ambion Inc. at Ambion's web site; and by other web-based design tools at, for example, the Invitrogen, Dharmacon, Integrated DNA Technologies, or Genscript web sites. Initial search parameters can include G/C contents between 35% and 55% and siRNA lengths between 19 and 27 nucleotides. The target sequence may be located in the coding region or in the 5' or 3' untranslated regions of the mRNA. The target sequences can be used to derive interfering RNA molecules, such as those described herein.

Interfering RNA target sequences (e.g., siRNA target sequences) within a target mRNA sequence are selected using available design tools as discussed above. Interfering RNAs corresponding to a target sequence are then tested in vitro by transfection of cells expressing the target mRNA followed by assessment of knockdown as described herein. The interfering RNAs can be further evaluated in vivo using animal models as described herein.

The ability of interfering RNA to knock-down the levels of endogenous target gene expression in, for example, HeLa cells can be evaluated in vitro as follows. HeLa cells are plated 24 h prior to transfection in standard growth medium (e.g., DMEM supplemented with 10% fetal bovine serum). Transfection is performed using, for example, Dharmafect 1 (Dharmacon, Lafayette, Colo.) according to the manufacturer's instructions at interfering RNA concentrations ranging from 0.1 nM-100 nM. SiCONTROL™ Non-Targeting siRNA #1 and siCONTROL™ Cyclophilin B siRNA (Dharmacon) are used as negative and positive controls, respectively. Target mRNA levels and cyclophilin B mRNA (PPIB, NM_000942) levels are assessed by qPCR 24 h post-transfection using, for example, a TAQMAN® Gene Expression Assay that preferably overlaps the target site (Applied Biosystems, Foster City, Calif.). The positive control siRNA gives essentially complete knockdown of cyclophilin B mRNA when transfection efficiency is 100%. Therefore, target mRNA knockdown is corrected for transfection efficiency by reference to the cyclophilin B mRNA level in cells transfected with the cyclophilin B siRNA. Target protein levels may be assessed approximately 72 h post-transfection (actual time dependent on protein turnover rate) by western blot, for example. Standard techniques for RNA and/or protein isolation from cultured cells are well-known to those skilled in the art. To reduce the chance of non-specific, off-target effects, the lowest possible concentration of interfering RNA is used that produces the desired level of knock-down in target gene expression. Human corneal epithelial cells or other human ocular cell lines may also be use for an evaluation of the ability of interfering RNA to knock-down levels of an endogenous target gene.

In certain embodiments, an interfering RNA delivery system comprises an interfering RNA molecule that targets a gene associated with an ocular disorder. Examples of mRNA target genes for which interfering RNAs of the present invention are designed to target include genes associated with the disorders that affect the retina, genes associated with glaucoma, and genes associated with ocular inflammation.

Examples of mRNA target genes associated with the retinal disorders include TEK tyrosine kinase, endothelial (TEK); complement factor B (CFB); hypoxia-inducible factor 1, α subunit (HIF1A); HtrA serine peptidase 1 (HTRA1); platelet-derived growth factor receptor β (PDGFRB); chemokine, CXC motif, receptor 4 (CXCR4); insulin-like growth factor I receptor (IGF1R); angiopoietin 2 (ANGPT2);

v-fos FBJ murine osteosarcoma viral oncogene homolog (FOS); cathepsin L1, transcript variant 1 (CTSL1); cathepsin L1, transcript variant 2 (CTSL2); intracellular adhesion molecule 1 (ICAM1); insulin-like growth factor I (IGF1); integrin α5 (ITGA5); integrin β1 (ITGB1); nuclear factor kappa-B, subunit 1 (NFKB1); nuclear factor kappa-B, subunit 2 (NFKB2); chemokine, CXC motif, ligand 12 (CXCL12); tumor necrosis factor receptor 1 (TNFR1); vascular endothelial growth factor (VEGF); vascular endothelial growth factor receptor 1 (VEGFR1); tumor necrosis factor-alpha-converting enzyme (TACE); and kinase insert domain receptor (KDR).

Examples of target genes associated with glaucoma include carbonic anhydrase II (CA2); carbonic anhydrase IV (CA4); carbonic anhydrase XII (CA12); β1 andrenergic receptor (ADBR1); β2 andrenergic receptor (ADBR2); acetylcholinesterase (ACHE); Na+/K+-ATPase; solute carrier family 12 (sodium/potassium/chloride transporters), member 1 (SLC12A1); solute carrier family 12 (sodium/potassium/chloride transporters), member 2 (SLC12A2); connective tissue growth factor (CTGF); serum amyloid A (SAA); secreted frizzled-related protein 1 (sFRP1); gremlin (GREM1); lysyl oxidase (LOX); c-Maf; rho-associated coiled-coil-containing protein kinase 1 (ROCK1); rho-associated coiled-coil-containing protein kinase 2 (ROCK2); plasminogen activator inhibitor 1 (PAT-1); endothelial differentiation, sphingolipid G-protein-coupled receptor, 3 (Edg3 R); myocilin (MYOC); NADPH oxidase 4 (NOX4); Protein Kinase Cδ (PKCδ); Aquaporin 1 (AQP1); Aquaporin 4 (AQP4); members of the complement cascade; ATPase, H+ transporting, lysosomal V1 subunit A (ATP6V1A); gap junction protein α-1 (GJA1); formyl peptide receptor 1 (FPR1); formyl peptide receptor-like 1 (FPRL1); interleukin 8 (IL8); nuclear factor kappa-B, subunit 1 (NFKB1); nuclear factor kappa-B, subunit 2 (NFKB2); presenilin 1 (PSEN1); tumor necrosis factor-alpha-converting enzyme (TACE); transforming growth factor β2 (TGFB2); transient receptor potential cation channel, subfamily V, member 1 (TRPV1); chloride channel 3 (CLCN3); gap junction protein α5 (GJA5); tumor necrosis factor receptor 1 (TNFR1); and chitinase 3-like 2 (CHI3L2).

Examples of mRNA target genes associated with ocular inflammation include tumor necrosis factor receptor superfamily, member 1A (TNFRSF1A); phosphodiesterase 4D, cAMP-specific (PDE4D); histamine receptor H1 (HRH1); spleen tyrosine kinase (SYK); interleukin 1β (IL1B); nuclear factor kappa-B, subunit 1 (NFKB1); nuclear factor kappa-B, subunit 2 (NFKB2); and tumor necrosis factor-alpha-converting enzyme (TACE).

Such target genes are described, for example, in U.S. patent applications having Publication Nos. 20060166919, 20060172961, 20060172963, 20060172965, 20060223773, 20070149473, and 20070155690, the disclosures of which are incorporated by reference in their entirety.

In certain embodiments, the invention provides a pharmaceutical composition comprising an interfering RNA delivery system of the invention. In certain embodiments, the composition is in a pharmaceutically acceptable carrier in a therapeutically effective amount.

Pharmaceutical compositions are formulations that comprise interfering RNAs, or salts thereof, of the invention up to 99% by weight mixed with a physiologically acceptable carrier medium, including those described infra, and such as water, buffer, saline, glycine, hyaluronic acid, mannitol, and the like.

Compositions of the present invention are administered as solutions, suspensions, or emulsions. The following are examples of pharmaceutical composition formulations that may be used in the methods of the invention.

|  | Amount in weight % |
|---|---|
| Interfering RNA | up to 99; 0.1-99; 0.1-50; 0.5-10.0 |
| Hydroxypropylmethylcellulose | 0.5 |
| Sodium chloride | 0.8 |
| Benzalkonium Chloride | 0.01 |
| EDTA | 0.01 |
| NaOH/HCl | qs pH 7.4 |
| Purified water (RNase-free) | qs 100 mL |

|  | Amount in weight % |
|---|---|
| Interfering RNA | up to 99; 0.1-99; 0.1-50; 0.5-10.0 |
| Phosphate Buffered Saline | 1.0 |
| Benzalkonium Chloride | 0.01 |
| Polysorbate 80 | 0.5 |
| Purified water (RNase-free) | q.s. to 100% |

|  | Amount in weight % |
|---|---|
| Interfering RNA | up to 99; 0.1-99; 0.1-50; 0.5-10.0 |
| Monobasic sodium phosphate | 0.05 |
| Dibasic sodium phosphate (anhydrous) | 0.15 |
| Sodium chloride | 0.75 |
| Disodium EDTA | 0.05 |
| Cremophor EL | 0.1 |
| Benzalkonium chloride | 0.01 |
| HCl and/or NaOH | pH 7.3-7.4 |
| Purified water (RNase-free) | q.s. to 100% |

|  | Amount in weight % |
|---|---|
| Interfering RNA | up to 99; 0.1-99; 0.1-50; 0.5-10.0 |
| Phosphate Buffered Saline | 1.0 |
| Hydroxypropyl-β-cyclodextrin | 4.0 |
| Purified water (RNase-free) | q.s. to 100% |

As used herein, the term "therapeutically effective amount" refers to the amount of interfering RNA or a pharmaceutical composition comprising an interfering RNA determined to produce a therapeutic response in a mammal. Such therapeutically effective amounts are readily ascertained by one of ordinary skill in the art and using methods as described herein.

Generally, a therapeutically effective amount of the interfering RNAs used in a composition of the invention results in an extracellular concentration at the surface of the target cell of from 100 pM to 1 µM, or from 1 nM to 100 nM, or from 5 nM to about 50 nM, or to about 25 nM. The dose required to achieve this local concentration will vary depending on a number of factors including the delivery method, the site of delivery, the number of cell layers between the delivery site and the target cell or tissue, whether delivery is local or systemic, etc. The concentration at the delivery site may be considerably higher than it is at the surface of the target cell or tissue. Topical compositions can be delivered to the surface of the target organ one to four times per day, or on an extended delivery schedule such as daily, weekly, bi-weekly, monthly, or longer, according to the routine discretion of a skilled clinician. The pH of the formulation is about pH 4.0 to about pH 9.0, or about pH 4.5 to about pH 7.4.

A therapeutically effective amount of a formulation may depend on factors such as the age, race, and sex of the subject, the severity of the disorder, the rate of target gene transcript/protein turnover, the interfering RNA potency, and the interfering RNA stability, for example. In one embodiment, the interfering RNA is delivered topically to a target organ and reaches the target mRNA-containing tissue at a therapeutic dose thereby ameliorating target gene-associated disease process.

Therapeutic treatment of patients with interfering RNAs directed against target mRNAs is expected to be beneficial over small molecule treatments by increasing the duration of action, thereby allowing less frequent dosing and greater patient compliance, and by increasing target specificity, thereby reducing side effects.

A "pharmaceutically acceptable carrier" as used herein refers to those carriers that cause at most, little to no irritation, provide suitable preservation if needed, and deliver one or more interfering RNAs of the present invention in a homogenous dosage.

The delivery systems and compositions of the present invention may be delivered in solution, in suspension, or in bioerodible or non-bioerodible delivery devices.

The delivery systems and compositions of the present invention may be delivered via absorption, adsorption, aerosol, buccal, dermal, inhaling, intracentricular, intracranial, intradermal, intramuscular, intranasal, intraocular, intrapulmonary, intravenous, intraperitoneal, intrasternal, intrathecal, intraventricular, nasal, ocular, oral, otic, parenteral, patch, rectal, systemic, subcutaneous, sublingual, topical, or transdermal, or vaginal administration, for example.

Interfering RNA delivery systems may be delivered directly to the eye by ocular tissue injection such as periocular, conjunctival, subtenon, intracameral, intravitreal, intraocular, anterior or posterior juxtascleral, subretinal, subconjunctival, retrobulbar, or intracanalicular injections; by direct application to the eye using a catheter or other placement device such as a retinal pellet, intraocular insert, suppository or an implant comprising a porous, non-porous, or gelatinous material; by topical ocular drops or ointments; or by a slow release device in the cul-de-sac or implanted adjacent to the sclera (transscleral) or in the sclera (intrascleral) or within the eye. Intracameral injection may be through the cornea into the anterior chamber to allow the agent to reach the trabecular meshwork. Intracanalicular injection may be into the venous collector channels draining Schlemm's canal or into Schlemm's canal.

For ocular administration, the compositions of the invention can be delivered by intravitreal injection every 2-6 weeks, for example, or via topical ocular, anterior or posterior juxtascleral depot, subconjunctival, periocular, retrobulbar, subtenon, intracameral, intraocular, subretinal, or suprachoroidal administration.

For pharmaceutical delivery, compositions of the present invention may be combined with pharmaceutically acceptable preservatives, co-solvents, surfactants, viscosity enhancers, penetration enhancers, buffers, sodium chloride, or water to form an aqueous, sterile suspension or solution. Solution formulations may be prepared by dissolving the conjugate in a physiologically acceptable isotonic aqueous buffer. Further, the solution may include an acceptable surfactant to assist in dissolving the interfering RNA. Viscosity building agents, such as hydroxymethyl cellulose, hydroxyethyl cellulose, methylcellulose, polyvinylpyrrolidone, or the like may be added to the compositions of the present invention to improve the retention of the compound.

In order to prepare a sterile ointment formulation, the composition is combined with a preservative in an appropriate vehicle, such as mineral oil, liquid lanolin, or white petrolatum. Sterile gel formulations may be prepared by suspending the composition of the invention in a hydrophilic base prepared from the combination of, for example, CARBOPOL®-940 (BF Goodrich, Charlotte, N.C.), or the like, according to methods known in the art. VISCOAT® (Alcon Laboratories, Inc., Fort Worth, Tex.) may be used for intraocular injection, for example. Other compositions of the present invention may contain penetration enhancing agents such as cremephor and TWEEN® 80 (polyoxyethylene sorbitan monolaureate, Sigma Aldrich, St. Louis, Mo.).

In certain embodiments, the invention also provides a kit that includes reagents for attenuating the expression of an mRNA as cited herein in a cell. The kit contains an interfering RNA molecule conjugated to a CPP-Arg or a CPP-HA2-Arg peptide and/or the necessary components for production of an interfering RNA molecule conjugated to a CPP-Arg or a CPP-HA2-Arg peptide (e.g., an interfering RNA molecule as well as the peptide and necessary materials for linking). The kit may also contain positive and negative control siRNAs or shRNA expression vectors (e.g., a non-targeting control siRNA or an siRNA that targets an unrelated mRNA). The kit also may contain reagents for assessing knockdown of the intended target gene (e.g., primers and probes for quantitative PCR to detect the target mRNA and/or antibodies against the corresponding protein for western blots). Alternatively, the kit may comprise an siRNA sequence or an shRNA sequence and the instructions and materials necessary to generate the siRNA by in vitro transcription or to construct an shRNA expression vector.

A pharmaceutical combination in kit form is further provided that includes, in packaged combination, a carrier means adapted to receive a container means in close confinement therewith and a first container means including an interfering RNA composition and a peptide. Such kits can further include, if desired, one or more of various conventional pharmaceutical kit components, such as, for example, containers with one or more pharmaceutically acceptable carriers, additional containers, etc., as will be readily apparent to those skilled in the art. Printed instructions, either as inserts or as labels, indicating quantities of the components to be administered, guidelines for administration, and/or guidelines for mixing the components, can also be included in the kit.

The references cited herein, to the extent that they provide exemplary procedural or other details supplementary to those set forth herein, are specifically incorporated by reference.

Those of skill in the art, in light of the present disclosure, will appreciate that obvious modifications of the embodiments disclosed herein can be made without departing from the spirit and scope of the invention. All of the embodiments disclosed herein can be made and executed without undue experimentation in light of the present disclosure. The full scope of the invention is set out in the disclosure and equivalent embodiments thereof. The specification should not be construed to unduly narrow the full scope of protection to which the present invention is entitled.

EXAMPLES

The following example, including the experiments conducted and results achieved is provided for illustrative purposes only and are not to be construed as limiting the invention.

Example 1

Delivery of Dy547-siRNA to GTM-3 Cells Using 9×Arg-Linked Pen7 Peptide

The ability of CPPs to facilitate cellular uptake of siRNA molecules was examined using a retro-inverso 7-amino acid fragment of penetratin (Pen7), conjugated to a Dy547-labeled siRNA (siGLO Cyclophilin B Control siRNA; Dharmacon, Lafayette, Colo.) via 9×Arg, for delivery to the glaucomatous trabecular meshwork cell line, GTM-3.

GTM-3 cells (Pang, I. H., et al., 1994 *Curr Eye Res.* 13:51-63) were transfected with Dy547-siRNA complexed with Pen7-9×Arg or with 9×Arg (negative control). The 9×Arg and Pen7-9×Arg peptides were purchased from Sigma (St. Louis, Mo.).

The sequence for Pen7-9×Arg was:

$K^{\dagger}K^{\dagger}W^{\dagger}K^{\dagger}M^{\dagger}R^{\dagger}R^{\dagger}GA^{\dagger}GR^{\dagger}R^{\dagger}R^{\dagger}R^{\dagger}R^{\dagger}R^{\dagger}R^{\dagger}$. (SEQ ID NO: 12)

The sequence for 9×Arg was:

9xArg: $R^{\dagger}R^{\dagger}R^{\dagger}R^{\dagger}R^{\dagger}R^{\dagger}R^{\dagger}R^{\dagger}R^{\dagger}$. (SEQ ID NO: 1)

A superscripted dagger ($\dagger$) to the right of the one-letter code symbol denotes the use of a D-amino acid isomer as opposed to the standard L-amino acid isomer.

The Dy547-siRNA was resuspended in 1× siRNA buffer, an aqueous solution of 20 mM KCl, 6 mM HEPES (pH 7.5), 0.2 mM $MgCl_2$. siRNA-peptide complexes were prepared at a 1:10 molar ratio of siRNA to peptide, and incubated for 30 minutes at room temperature. The siRNA-peptide complexes were applied to GTM-3 cells in serum-free medium at a final siRNA concentration of 400 nM. After 4 hours, the medium was replaced with DMEM supplemented with 10% FBS. After 24 hours, the cells were harvested, and uptake of Dy547-siRNA was measured in a LSRII flow cytometry (BD Biosciences, Franklin Lakes, N.J.).

As shown in FIG. 1, GTM-3 cells were labeled only slightly by the Dy547-siRNA in the absence of a peptide (FIG. 1B) relative to non-treated cells (FIG. 1A). Addition of the 9×Arg peptide to the Dy547-siRNA did not enhance uptake (FIG. 1C) relative to the Dy547-siRNA alone (FIG. 1B). In contrast, Pen7-9×Arg peptide enhanced uptake of the Dy547-siRNA significantly, causing an increased fluorescence signal in approximately 88% of the cells (FIG. 1D).

These results demonstrated that linkage of siRNAs to CPP peptides facilitated siRNA delivery to cultured cells.

It should be understood that the foregoing disclosure emphasizes certain specific embodiments of the invention and that all modifications or alternatives equivalent thereto are within the spirit and scope of the invention as set forth in the appended claims.

---

What is claimed is:

1. An interfering RNA delivery system comprising an interfering RNA molecule linked to a cell penetrating peptide (CPP)-Arg peptide wherein the CPP-Arg peptide comprises the sequence as set forth in SEQ ID NO: 3.

2. The delivery system of claim 1, wherein the CPP-Arg peptide further comprises an HA2 peptide.

3. The delivery system of claim 1, wherein the interfering RNA molecule is linked to the CPP-Arg peptide via a covalent bond.

4. The delivery system of claim 1, wherein the interfering RNA molecule is a siRNA, miRNA, or shRNA.

5. A pharmaceutical composition comprising the delivery system of claim 1 and a pharmaceutically acceptable carrier.

6. A method of treating an ocular disorder in a patient, comprising administering to the patient the interfering RNA delivery system of claim 1, wherein the interfering RNA molecule can attenuate expression of a gene associated with the ocular disorder.

7. A method of delivering an interfering RNA molecule into a cell, comprising:

(a) attaching an interfering RNA molecule to a CPP-Arg peptide wherein the CPP-Arg peptide comprises the sequence as set forth in SEQ ID NO: 3, thereby forming an interfering RNA delivery system; and (b) administering the interfering RNA delivery system to the cell under conditions suitable for the system to enter the cell.

8. The method of claim 7, wherein release of the system from the endosome inside the cell is enhanced in the presence of an HA2 peptide.

9. The method of claim 8, wherein the HA2 peptide is introduced into the cell by administration of a CPP-HA2 peptide.

10. The method of claim 7, wherein the CPP-Arg peptide further comprises the HA2 peptide.

11. The method of claim 7, wherein the interfering RNA molecule is linked to the CPP-Arg peptide via a covalent bond.

12. The method of claim 7, wherein the interfering RNA molecule is a siRNA, miRNA, or shRNA.

* * * * *

SEQUENCE LISTING

```
<160> NUMBER OF SEQ ID NOS: 12

<210> SEQ ID NO 1
<211> LENGTH: 9
<212> TYPE: PRT
<213> ORGANISM: Artificial
<220> FEATURE:
<223> OTHER INFORMATION: Synthetic peptide

<400> SEQUENCE: 1

Arg Arg Arg Arg Arg Arg Arg Arg Arg
1               5

<210> SEQ ID NO 2
<211> LENGTH: 11
<212> TYPE: PRT
<213> ORGANISM: Artificial
<220> FEATURE:
<223> OTHER INFORMATION: Synthetic peptide

<400> SEQUENCE: 2

Tyr Gly Arg Lys Lys Arg Arg Gln Arg Arg Arg
1               5                   10

<210> SEQ ID NO 3
<211> LENGTH: 10
<212> TYPE: PRT
<213> ORGANISM: Artificial
<220> FEATURE:
<223> OTHER INFORMATION: Synthetic peptide

<400> SEQUENCE: 3

Arg Arg Arg Gln Arg Arg Lys Lys Arg Gly
1               5                   10

<210> SEQ ID NO 4
```

```
<211> LENGTH: 16
<212> TYPE: PRT
<213> ORGANISM: Artificial
<220> FEATURE:
<223> OTHER INFORMATION: Synthetic peptide

<400> SEQUENCE: 4

Arg Gln Ile Lys Ile Trp Phe Gln Asn Arg Arg Met Lys Trp Lys Lys
1               5                   10                  15

<210> SEQ ID NO 5
<211> LENGTH: 26
<212> TYPE: PRT
<213> ORGANISM: Artificial
<220> FEATURE:
<223> OTHER INFORMATION: Synthetic peptide

<400> SEQUENCE: 5

Leu Ile Lys Lys Ala Leu Ala Ala Leu Ala Lys Leu Asn Ile Lys Leu
1               5                   10                  15

Leu Tyr Gly Ala Ser Asn Leu Thr Trp Gly
            20                  25

<210> SEQ ID NO 6
<211> LENGTH: 27
<212> TYPE: PRT
<213> ORGANISM: Artificial
<220> FEATURE:
<223> OTHER INFORMATION: Synthetic peptide

<400> SEQUENCE: 6

Gly Ala Leu Phe Leu Gly Phe Leu Gly Ala Ala Gly Ser Thr Met Gly
1               5                   10                  15

Ala Trp Ser Gln Pro Lys Lys Lys Arg Lys Val
            20                  25

<210> SEQ ID NO 7
<211> LENGTH: 27
<212> TYPE: PRT
<213> ORGANISM: Artificial
<220> FEATURE:
<223> OTHER INFORMATION: Synthetic peptide

<400> SEQUENCE: 7

Gly Ala Leu Phe Leu Gly Phe Leu Gly Ala Ala Gly Ser Thr Met Gly
1               5                   10                  15

Ala Trp Ser Gln Pro Lys Ser Lys Arg Lys Val
            20                  25

<210> SEQ ID NO 8
<211> LENGTH: 37
<212> TYPE: PRT
<213> ORGANISM: Artificial
<220> FEATURE:
<223> OTHER INFORMATION: Synthetic peptide

<400> SEQUENCE: 8

Ala Cys Glu Gln Asn Pro Ile Tyr Trp Ala Arg Tyr Ala Asp Trp Leu
1               5                   10                  15

Phe Thr Thr Pro Leu Leu Leu Leu Asp Leu Ala Leu Leu Val Asp Ala
            20                  25                  30

Asp Glu Gly Thr Gly
        35
```

-continued

```
<210> SEQ ID NO 9
<211> LENGTH: 20
<212> TYPE: PRT
<213> ORGANISM: Artificial
<220> FEATURE:
<223> OTHER INFORMATION: Synthetic peptide

<400> SEQUENCE: 9

Gly Leu Phe Gly Ala Ile Ala Gly Phe Ile Glu Asn Gly Trp Glu Gly
1               5                   10                  15

Met Ile Asp Gly
            20

<210> SEQ ID NO 10
<211> LENGTH: 42
<212> TYPE: PRT
<213> ORGANISM: Artificial
<220> FEATURE:
<223> OTHER INFORMATION: Synthetic peptide

<400> SEQUENCE: 10

Arg Arg Arg Gln Arg Arg Lys Lys Arg Gly Gly Gly Asp Ile Met Gly
1               5                   10                  15

Glu Trp Gly Asn Glu Ile Phe Gly Ala Ile Ala Gly Phe Leu Gly Gly
                20                  25                  30

Gly Arg Arg Arg Arg Arg Arg Arg Arg Arg
            35                  40

<210> SEQ ID NO 11
<211> LENGTH: 42
<212> TYPE: PRT
<213> ORGANISM: Artificial
<220> FEATURE:
<223> OTHER INFORMATION: Synthetic peptide

<400> SEQUENCE: 11

Arg Arg Arg Gln Arg Arg Lys Lys Arg Gly Gly Gly Asp Ile Met Gly
1               5                   10                  15

Glu Trp Gly Asn Glu Ile Phe Gly Ala Ile Ala Gly Phe Leu Gly Gly
                20                  25                  30

Gly Arg Arg Arg Arg Arg Arg Arg Arg Arg
            35                  40

<210> SEQ ID NO 12
<211> LENGTH: 19
<212> TYPE: PRT
<213> ORGANISM: Artificial
<220> FEATURE:
<223> OTHER INFORMATION: Synthetic peptide

<400> SEQUENCE: 12

Lys Lys Trp Lys Met Arg Arg Gly Ala Gly Arg Arg Arg Arg Arg
1               5                   10                  15

Arg Arg Arg
```